United States Patent

Ceriale

Patent Number: 5,676,012
Date of Patent: Oct. 14, 1997

[54] PROCESS FOR FORMING ENDOSCOPIC SHAVER BLADE FROM ELONGATE TUBE

[75] Inventor: James M. Ceriale, Green Oaks, Ill.

[73] Assignee: Spectrum Manufacturing, Inc., Wheeling, Ill.

[21] Appl. No.: 567,293

[22] Filed: Dec. 5, 1995

[51] Int. Cl.$^6$ ........................................ B21D 9/04
[52] U.S. Cl. ........................... 72/294; 72/339; 72/370; 606/170
[58] Field of Search ........................ 72/370, 367, 318, 72/293, 316, 324, 339, 359, 294; 29/890.142, 890.143; 606/170, 171, 179

[56] References Cited

U.S. PATENT DOCUMENTS

| | | |
|---|---|---|
| 934,174 | 9/1909 | Hooker ........................ 72/370 |
| 1,133,017 | 3/1915 | Frandsen ..................... 72/367 |
| 2,284,210 | 5/1942 | Johnson ...................... 72/370 |
| 2,421,887 | 6/1947 | Huthsing .................. 29/890.143 |
| 2,971,554 | 2/1961 | Knox ........................ 72/316 |
| 3,618,611 | 11/1971 | Urban. | 
| 3,732,858 | 5/1973 | Banko. |
| 3,945,375 | 3/1976 | Banko. |
| 3,996,935 | 12/1976 | Banko. |
| 4,157,977 | 6/1979 | Frost. |
| 4,167,944 | 9/1979 | Banko. |
| 4,203,444 | 5/1980 | Bonnell et al.. |
| 4,210,146 | 7/1980 | Banko. |
| 4,274,414 | 6/1981 | Johnson et al.. |
| 4,368,734 | 1/1983 | Banko. |
| 4,512,344 | 4/1985 | Barber. |
| 4,598,710 | 7/1986 | Kleinberg et al.. |
| 4,603,694 | 8/1986 | Wheeler. |
| 4,649,919 | 3/1987 | Thimsen et al.. |
| 4,660,267 | 4/1987 | Wheeler. |
| 4,834,729 | 5/1989 | Sjostrom. |
| 4,850,354 | 7/1989 | McGurk et al.. |
| 4,867,157 | 9/1989 | McGurk et al.. |
| 4,955,882 | 9/1990 | Hakky. |
| 5,007,917 | 4/1991 | Evans. |
| 5,084,052 | 1/1992 | Jacobs. |
| 5,112,299 | 5/1992 | Pascaloff. |
| 5,165,168 | 11/1992 | Higgins ...................... 72/367 |
| 5,217,479 | 6/1993 | Shuler. |
| 5,269,798 | 12/1993 | Winkler. |
| 5,292,330 | 3/1994 | Shutt. |
| 5,324,301 | 6/1994 | Drucker. |
| 5,364,395 | 11/1994 | West. |
| 5,376,078 | 12/1994 | Dinger et al.. |
| 5,383,884 | 1/1995 | Summers. |
| 5,395,313 | 3/1995 | Haves. |
| 5,437,630 | 8/1995 | Daniel et al.. |

FOREIGN PATENT DOCUMENTS

| | | |
|---|---|---|
| 9208416 | 5/1992 | European Pat. Off.. |
| 2848314 | 5/1979 | Germany. |
| 3828478 | 5/1989 | Germany. |
| 4310421 | 10/1994 | Germany. |
| 2087239 | 5/1982 | United Kingdom. |

OTHER PUBLICATIONS

Smith & Nephew Dynics–Identification Chart.

Primary Examiner—Daniel C. Crane
Attorney, Agent, or Firm—George Pappas

[57] ABSTRACT

A process of forming a one piece weld free endoscopic shaver blade from an elongate metal cylindrical tube includes first cutting the tube first distal end to a predefined opening shape. A mandrel is inserted into the longitudinal tube with its working end adjacent the tube distal end. The tube distal end is further supported and a first die is forced thereon in a direction generally perpendicular to the elongate tube and forming the tube end and defining a shaver blade opening. A second die is forced onto the tube first distal end in a direction generally parallel to the tube longitudinal further forming the tube end and shaver blade opening. The formed shaver blade opening is then machined or edge-formed as needed to a final shaver blade opening and perimeter shape.

22 Claims, 3 Drawing Sheets

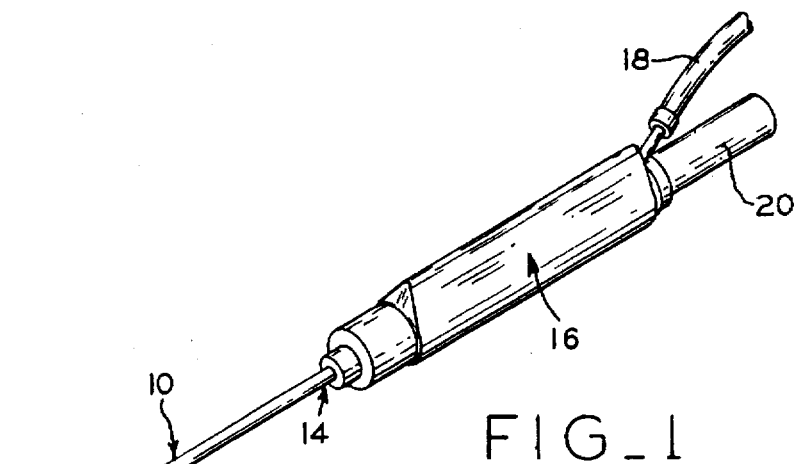
FIG_1
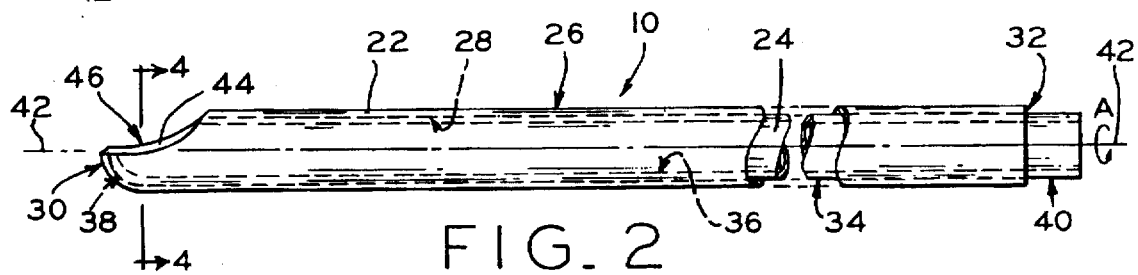
FIG_2
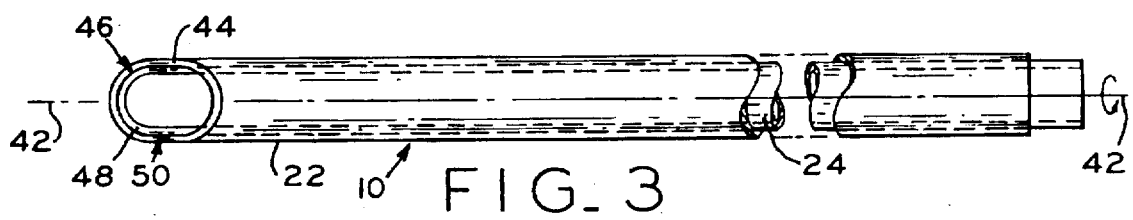
FIG_3
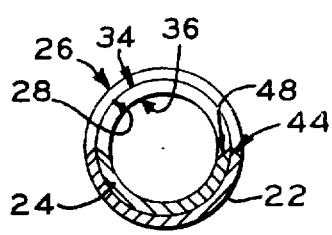
FIG_4
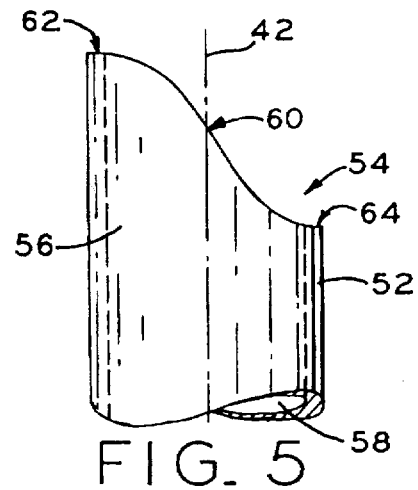
FIG_5

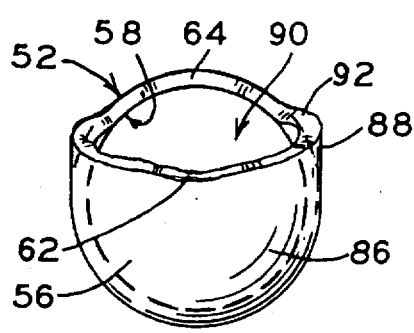
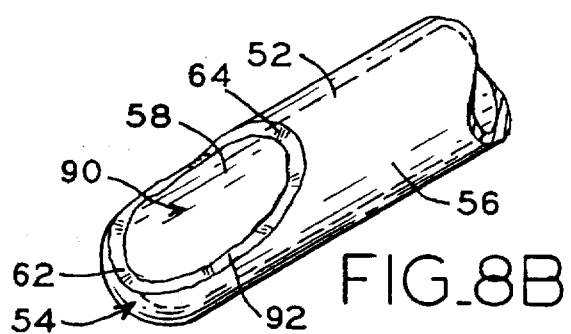
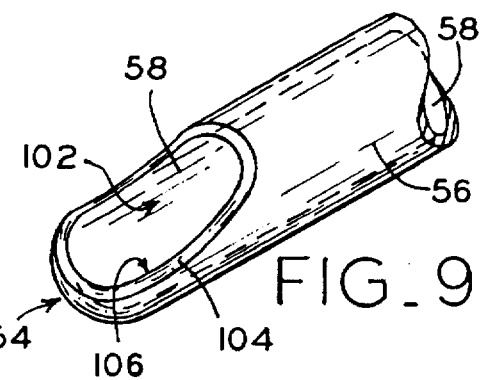
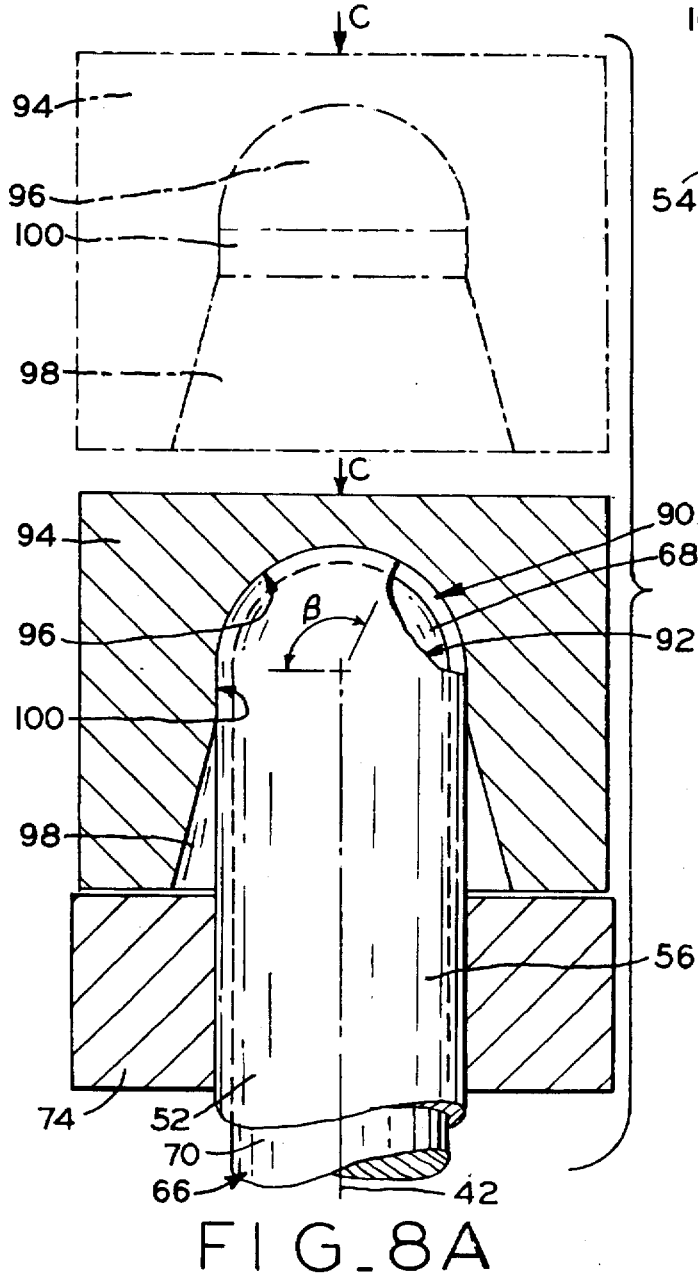
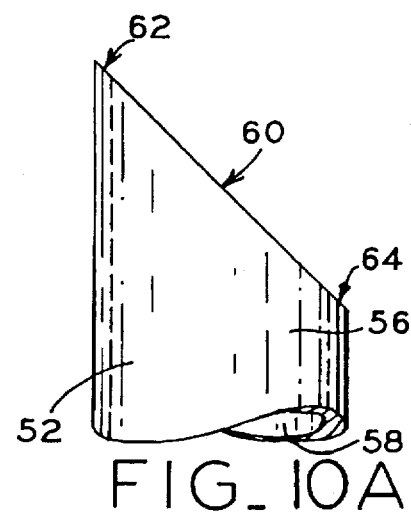

5,676,012

PROCESS FOR FORMING ENDOSCOPIC SHAVER BLADE FROM ELONGATE TUBE

TECHNICAL FIELD

The present invention relates to the technical field of endoscopic or minimal invasion surgery instruments. More specifically, the present invention relates to a process of efficiently and inexpensively manufacturing highly reliable endoscopic surgery blades from stainless steel metal tubes.

BACKGROUND OF THE INVENTION

Endoscopic surgery, also known as arthroscopic or minimal invasion surgery, has currently become very common practice. Typically, an incision or hole is made and an endoscopic blade is inserted therethrough to a desired location such as the patient's knee, shoulders, elbows, sinuses, etc., whereat, the endoscopic blade is used for removing tissue or roughing an area as needed by the doctor or surgeon. Quite often, two other incisions are made wherethrough an air source is provided into the patient for expanding the work area and, also, a camera is provided within the work area for providing the doctor with a view thereof.

One type of endoscopic surgical instrument, also known as a shaver blade, consists of an outer stationary tube member having a distal aperture and an inner rotatably driven tube member disposed within the outer tube member and also having a distal aperture. Both of the tube members are supported on a control handle assembly which is grasped by the surgeon for controlling and manipulating the blade as needed. The perimeters of the inner and outer tube member apertures are shaped in a manner whereby a scissor cutting action is provided between the inner and outer aperture perimeters as the inner tube member is rotated about its longitudinal axis within the stationary outer member. Accordingly, by manipulating the blade, tissue received within both of the apertures is cut between the respective aperture perimeter cutting edges. Suction is provided within the inner rotating member for withdrawing and disposing the tissue up through the inner rotating member and the surgical instrument control handle. After use, the shaver blades are typically detached from the handle assembly and are discarded or otherwise disposed.

One preferred type of endoscopic surgery blade is provided with a sphere shaped distal end and a cutting aperture located close to or starting at the distal sphere shape and generally opening in a direction transverse to the longitudinal. The sphere shaped distal end is readily insertable through incisions and around tissue and organs while providing the cutting aperture at a location for maximizing control.

Prior endoscopic blades having a sphere and/or other shaped distal ends have been manufactured by first creating a distal end portion by machining and other cutting operations. That is, the distal end portions of either the inner or outer blades are machined from a piece of stainless steel by machining operations such as drilling, electrical discharge machines, lathes, etc., thereby forming the spheric end, apertures and cutting edges. Thereafter, to provide the needed longitudinal length, the small distal end portion is welded onto the end of a tube having a corresponding inner and outer diameter. The same process is used for both the outer stationary member and the inner rotating member except that the distal end portion and tubes are varied in diameter as needed.

Another prior method of manufacturing endoscopic blades has been to first swag or otherwise form the stainless steel metal end of a tube into a half sphere. That is, the metal of a tube end is forced radially inwardly toward the longitudinal center of the tube and onto a mandrel within the tube. However, because the metal cannot be swaged into a perfect sphere and a hole remains, the hole at the very distal end is filled by a small bead of weld thereby closing the tip and forming the spheric end. Thereafter, the weld is machined as may be needed for smoothing, the aperture is cut into the distal end, and the cutting edges are formed as needed by machining operation.

The prior methods of manufacturing, however, have shortcomings and drawbacks. In general, both methods are significantly time consuming and costly to implement in a manner whereby the precision and required tolerances can be consistently maintained as needed. This is especially critical in view of the shaver blade operational requirements during which the inner blade is rotated up to 6000 revolutions per minute. More importantly, both prior art methods of manufacturing require a welding operation which, quite often, cannot consistently be provided reliably thereby providing a blade construction which is liable to fail and/or otherwise break apart while in use. As can be appreciated, failures of shaver blades while in use within a patient can be severely problematic.

Accordingly, a need exists for endoscopic surgery blades that can be manufactured quickly and inexpensively with the required precision and tolerances and which, further, are consistently highly reliable and are less apt to fail during normal use.

SUMMARY OF THE INVENTION

It is the principal object of the present invention to overcome the above-discussed disadvantages associated with prior endoscopic surgery blades and methods of manufacturing the same.

The present invention overcomes the disadvantages associated with prior endoscopic surgery blades by providing a weld free process of manufacturing endoscopic surgery blades. The process utilizes common stock stainless steel tubing material. Initially, a first longitudinal end of a tube is cut for creating an opening that extends between an outside area located longitudinally apart from an inside area. Preferably, the longitudinal distance between the inside and outside areas or points on the tube are at least as far apart as the inside radius of the elongate tube.

After the cutting step, a mandrel having a generally sphere shaped working end is inserted into the tube with the working end adjacent the tube opening. The sphere shaped working end includes an annular area of tangency whereat the sphere shaped working end meets the rod shaped mandrel body. The mandrel is located with the annular area of tangency being adjacent the tube longitudinal end inside area. A supporting die is then placed around the elongate tube near the longitudinal end for supporting the tube and mandrel.

After supporting the stainless steel tube with the supporting die, a first die also having a generally sphere shape is forced onto the tube first longitudinal end and the mandrel working end in a direction generally perpendicular with respect to the tube longitudinal axis. The first die shapes and forces the tube material located longitudinally between the outside and inside areas in a perpendicular direction and thereby forming a half sphere. Preferably, the outside area of the tube is located coplanar with the perpendicular direction of motion of the first die. Thus, a half sphere is formed on the mandrel working end and any excess tube material extends perpendicularly beyond the mandrel surface in planes that are generally parallel with the direction of motion of the first die and forming a cylindrical shape.

A second die, also having a generally sphere shape, is then forced onto the tube longitudinal end and mandrel working end in a direction substantially parallel to the tube longitudinal axis. The second die shape pushes and forms any excess tube material onto the sphere shaped mandrel working end, thereby forming a shaver blade distal end having a sphere shape which extends beyond 90 degrees or the longitudinal axis as viewed from the side and, further, wherein a shaver blade opening is defined facing in a direction generally perpendicularly from the longitudinal axis. More specifically, the new shaver blade opening extends, as viewed from the side, from the previously defined inside area to the location whereat the previously defined outside area has been pushed.

By having cut the tube end with a previously defined shape the resultant shaver blade opening, after forcing the first and second dies thereon, can be shaped substantially as needed or desired. However, because the forming of the tube material via the first and second dies is not always as precise as may be needed, the shaver blade opening perimeter is edgeformed for providing a more exact shape and sharpening as needed. The edgeforming process is completed by grinding, electrical discharge machining, cutting, etc.

Both of the inside and outside shaver blade members are formed using the same process. The respective tube inside and outside diameters are chosen for providing a tight but sliding fit between the outside surface of the inner tube member and the inside surface of the outer tube member. Additionally, the tube lengths are varied by merely cutting the opposite longitudinal end either before and/or after the forming process to any desired length as may be needed.

In one form thereof, the present invention is directed to a process of forming an endoscopic shaver blade from an elongate metal cylindrical tube having a longitudinal axis, a first longitudinal end, and second longitudinal end opposite the first end. The process includes a first step of cutting the tube first longitudinal end for creating an opening extending between an outside area located longitudinally apart from an inside area. The outside area is located furthest from the tube second longitudinal end. Thereafter, a mandrel having a working end is inserted into the tube with the working end adjacent the tube opening. A first die shape is then forced onto the tube first longitudinal end and the mandrel working end and thereby forming the tube first longitudinal end therebetween and creating a shaver blade opening.

BRIEF DESCRIPTION OF THE DRAWINGS

The above-mentioned and other features and objects of this invention and the manner of obtaining them will become more apparent and the invention itself will be better understood by reference to the following description of embodiments of the invention taken in conjunctions with the accompanying drawings wherein:

FIG. 1 is a perspective view of a set of endoscopic shaver blades constructed in accordance with the principles of the present invention and shown mounted on a control handle assembly;

FIG. 2 is a side elevation view showing a set of shaver blades constructed in accordance with the principles of the present invention;

FIG. 3 is a top plan view of the set of shaver blades shown in FIG. 2.

FIG. 4 is cross sectional view of the set of shaver blades shown in FIG. 2 taken along line 4—4;

FIG. 5 is a side elevation view of a distal end of a metal tube that has been cut in accordance with the principles of the present invention;

FIG. 7c is an end view of the tube longitudinal end after the forming step as shown in FIG. 7a;

FIG. 8a is a side elevation view showing and depicting the forcing of a second die onto the tube end and mandrel working end in a direction parallel to the longitudinal axis;

FIG. 8b is a perspective view of the tube end after the forming step of FIG. 8a;

FIG. 9 is a perspective view of the tube end shown in FIG. 8b and wherein the perimeter of the previously formed shaver blade opening has been edgeformed and/or sharpened; and, FIG. 10a is a side elevation view of an alternate cutting shape of a tube end prior to subjecting it to the first and second die forming steps.

Corresponding reference characters indicate corresponding parts throughout the several views of the drawings.

Figure 6:
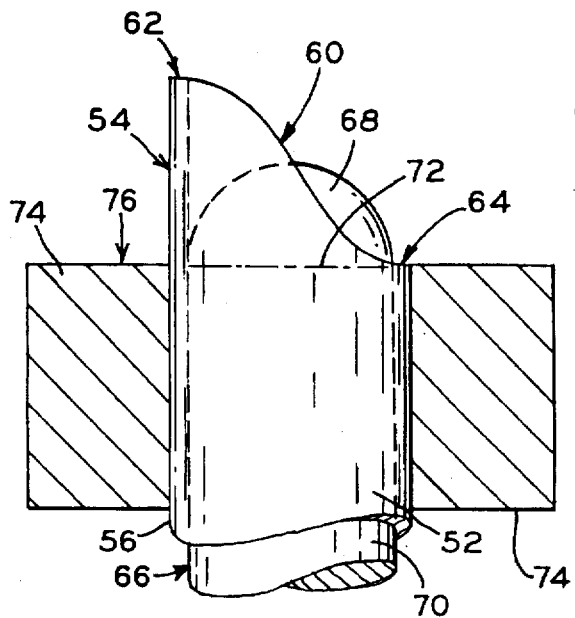
FIG. 6 is a side elevation view of the tube distal end shown in FIG. 5 and, further, wherein a mandrel is inserted within the tube and a supporting die, shown in cross-section, is placed on the outside of the tube end.

The exemplifications set out herein illustrate preferred embodiments of the invention in one form thereof and such exemplifications are not to be construed as limiting the scope of the disclosure or the scope of the invention in any manner.

DETAILED DESCRIPTION OF THE PREFERRED EMBODIMENTS

Referring initially to FIG. 1, there is shown a set endoscopic surgery shaver blades generally depicted by the numeral 10 including shaver blade apertures or openings at their distal ends 12. At their other or second end 14, shaver blades 10 are mounted and/or supported on a control handle assembly 16 which is provided with a suction hose 18 and an electrical or pneumatic power source 20. Control handle assembly 16 is provided in a known and customary manner for detachably attaching shaver blades 10 thereto and for selectively rotatably driving the inner blade while retaining the outer blade stationary.

A set of shaver blades 10 constructed in accordance with the principles of the present invention are shown in FIGS. 2–4. The set of shaver blades 10 includes an outer stationary stainless steel tube member 22 and an inner rotatably driven stainless steel tube member 24. Outer tube member 22 includes an outer surface 26, inner surface 28, a first distal end 30 whereat a shaver blade opening or aperture is provided, and a second back distal end 32. Inner tube member 24 is nearly identical to outer tube member 22 and includes an outer surface 34, inner surface 36, first distal end 38 whereat a shaver blade opening or aperture is provided, and a second back distal end 40. Inner tube member 24 is typically longitudinally longer than outer tube member 22 as shown so as to be coupled, in a known customary manner, and rotatably driven about longitudinal axis 42 as indicated by arrow A. The outer diameter of inner tube member 24 is slightly smaller than the inner diameter of outer tube member 22 such that inner tube member 24 freely rotates therein without substantial friction.

Both first distal ends 30 and 38 of tube members 22 and 24 are preferably partially sphere shaped as shown. Outer tube member 22 includes a shaver blade opening or aperture defined by a perimeter surface 44. Perimeter surface 44 is preferably at an angle with respect to outer surface 26 and inner surface 28 so as to form a scissor cutting line 46. The inner tube member shaver blade opening or aperture is defined by a perimeter surface 48, also at an angle with respect to the tube outer surface 34 and inner surface 36, thereby defining a scissor cutting line 50. Thus, in operation, any tissue received in the aperture of inner tube member 24 is selectively cut as the inner tube perimeter surface 48 and cutting line 50 slidingly travel adjacent the outer tube member perimeter surface 44 and cutting line 46.

Referring now more particularly to FIGS. 5–10, the preferred process of forming an outer tube member 22 or inner tube member 24 will be described. It should be understood that both the inner tube member 24 and outer tube member 22 are made by a substantially similar process and, further that, although a sphere shaped distal end is shown being formed, the inventive process is not so limited and is intended for use in forming other shapes as may be needed.

Initially, as shown in FIG. 5, a steel tube 52 preferably made of stainless steel and having a desired inner and outer diameter, is cut to a desired length with a distal end 54 and an opposite second distal end (not shown). Tube member 52 has an outer surface 56 and an inner surface 58. Further, at its first distal end 54 tube member 52 is cut for creating an opening 60 extending between an outside area 62 and an inside area 64. As best seen in the side elevation view of FIG. 5, opening 60 opens in a direction generally perpendicular to longitudinal axis 42 and is sinusoidal shaped. As more fully described hereinbelow, the sinusoidal shape is determinative of the final shape of the shaver blade opening and can be selectively varied as may be needed to achieve a desired shaver blade opening at the end of the process. In most cases however, it is preferred that the outside area 62 be apart from the inside area 64 a distance longitudinally at least as far as the radius of the inside diameter of elongate tube 52.

After the first distal end 54 of tube 52 has been cut with an opening 60 of a desired predefined shaped, a mandrel 66 having a sphere shaped working end 68 is inserted into tube member 52 placing the sphere shaped working end 68 adjacent the tube opening 60. Mandrel 66 preferably includes a rod shaped body 70 and sphere shaped working end 68 includes or meets rod shaped body 70 at an annular area of tangency depicted by a long short dash line 72. Preferably, mandrel 66 is located within tube member 52 with the annular area of tangency 72 located adjacent inside area 64 and, most preferably, the annular area of tangency 72 is located longitudinally aligned with inside area 64 or inbetween inside area 64 and outside area 62. The outside diameter of mandrel 66 is preferably only slightly smaller than the inside diameter of tube member 52 for providing maximum stability and strength as needed in the following steps of the forming process.

For further stabilizing the tube first distal end 54, a supporting die 74, shown in FIG. 6 in cross-section, is provided and is placed around the outside of elongate tube member 52 as shown. Supporting die 74 can be constructed in several pieces for placement on tube member 52 with a clamping action or can be a block with a bore having a diameter slightly larger than the outside diameter of tube member 52 and placed thereon by inserting the tube member 52 and mandrel 66 therethrough. Most preferably, supporting die 74 surrounds the entire outer surface of tube member 52 and, further, is initially placed longitudinal as shown in FIG. 6 with the supporting die upper surface 76 generally coplanar with inside area 64 and annular area of tangency 72.

Figure 7B:
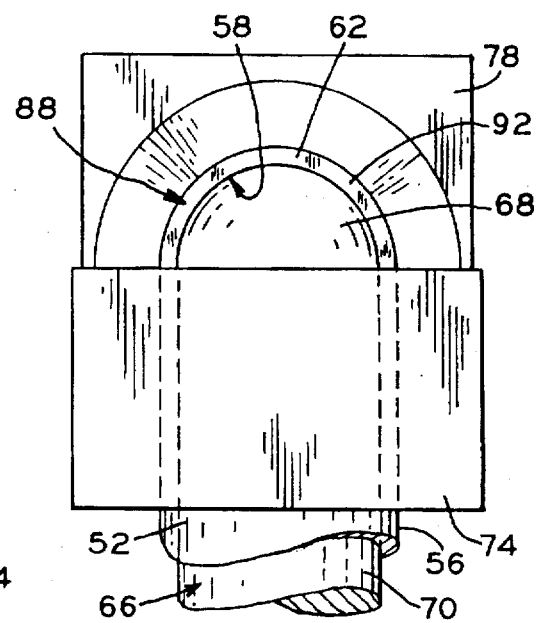
FIG. 7b is an end view of the assembly shown in FIG. 7a and taken along line 7b—7b.
Figure 7A:
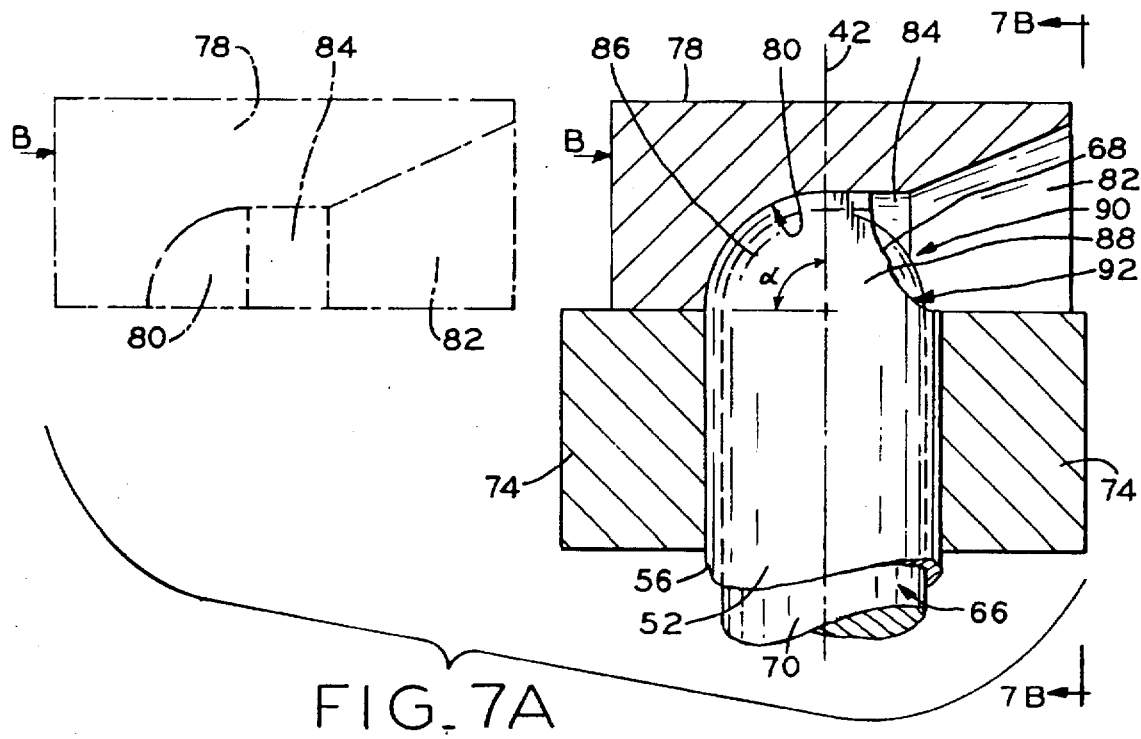
FIG. 7a is a side elevation view of the assembly shown in FIG. 6 and, further, wherein a first die is depicted and shown being forced onto the tube end and mandrel in a direction perpendicular to the longitudinal axis.

Referring now to FIG. 7a, after the first distal end 54 of tube member 52 is supported as discussed hereinabove, a first die 78 is moved or forced over and onto the tube distal end 54 in a substantially perpendicular direction to the tube longitudinal axis 42. More specifically, the first die 78 is moved as indicated from the position shown in the long short dash lines in the direction of arrows B to the position shown in solid lines. First die member 78 is shown in cross-section and includes a generally sphere shaped die surface area 80 communicating with a frusto-conical shaped lead in die surface area 82. A generally cylindrical shaped die surface area 84 may also be included between and communicating with the sphere shaped die surface area 80 and the frusto-conical lead in die shaped surface area 82.

In operation, as first die 78 is moved perpendicularly, the stainless steel material of tube 52 located between outside area 62 and inside area 64 is first wiped by frusto-conical die surface 82, thereby starting the forming process. Thereafter, as first die 78 is further moved or forced perpendicularly to its final position as shown in FIGS. 7a and 7b, the stainless steel material between outside area 62 and inside area 64 is further formed into a partial or half sphere shape designated by the angle α of about 90 degrees. That is, in the final position of first die 78 a half sphere 86 is sandwiched between mandrel working end 68 and the first die sphere shaped surface area 80. The remaining material indicated by the numeral 88, remains generally in contact with cylindrical shaped die surface area 84 but is not in contact with the sphere shaped working end 68 of mandrel 66. This remaining material 88 is, thus, also generally cylindrically shaped and terminates at a shaver blade opening 90. Preferably, prior to forcing the first die 78 thereon, tube member 52 is turned about its axis 42 placing outside area 62 in a position generally coplanar with the perpendicular direction of motion of first die 78.

In the event that only a half sphere shaped shaver blade is needed, tube member 52 is merely removed and shaver blade opening 90 is edgeformed by machining, electrical discharge, or other cutting processes to a desired shape and/or cutting surfaces.

Where the shaver blade distal end is required to have a sphere or shape other than the generally cylindrical shape whereat the remaining material 88 is located, an additional step of forming as depicted in FIG. 8a is provided. More specifically, a second die 94, also shown in cross-section, is provided and includes a sphere shaped die surface area 96, a frusto-conical lead in die surface area 98, and a cylindrical shaped die surface area 100 located between and communicating with the sphere shaped die surface area 96 and the cylindrical shaped die surface area 100. Here, supporting die 74 is first slipped longitudinally away from the first distal end 54 thereby exposing a greater longitudinal length thereof. Thereafter, the second die member 94 is moved or forced in a direction generally parallel with the tube longitudinal axis 42 as depicted by arrows C from a position shown in long short dash lines to a position as shown in solid lines. During this step, in general, the material forming the half sphere 86 is retained in place while the remaining material 88 is shaped and formed onto the mandrel sphere shaped working end 68. That is, as the second die 94 is moved longitudinally onto the first distal end 54 and mandrel 66, the remaining material 88 is initially wiped and then formed to a position as shown whereat it is sandwiched between the sphere shaped working end 68 and the sphere shaped die surface area 96. Thus, remaining material 88 also becomes generally sphere shaped for providing a distal end with a partial sphere extending to greater than 90 degrees or, as shown in FIG. 8a, to an angle of approximately β. This resulting shape is shown in FIG. 8b whereat the shaver blade opening 90 is defined by a perimeter surface 92 and the first distal end 54 of tube member 52 includes a partial sphere shape that extends over 90 degrees as viewed in a side elevation.

Finally, the shaver blade opening 90 and the perimeter surface 92 thereof are cut as needed or desired and shaped by electrical discharge, machine cutting, grinding and other machining processes as needed for creating the final desired shaver blade opening 102 and perimeter cutting surface 104. Also, the second or back distal end of tube member 52 (not shown) is cut and/or otherwise machined as may be desired for providing an overall longitudinal length of tube member 52 as needed.

In FIG. 10a there is shown an alternative cutting shape for opening 60 inbetween outside area 62 and inside area 64. Here, opening 60 is cut in a straight line and at an angle with respect to the longitudinal axis as viewed in side elevation. This depicts another one of the many different opening shapes contemplated for obtaining a shaver blade opening 90 of a desired shape. As can be appreciated, by cutting opening 60 to a predefined shape the shaver blade opening 90 formed after the steps of FIGS. 7a and/or FIG. 8a can be predicted for obtaining a desired result and, thereby, decreasing the edgeforming and other machining operations needed thereafter for achieving the final shaver blade opening 102. Indeed, it is desired that the shape of opening 60 be such that the resultant shaver blade opening 90 only requires, for example, a grinding operation to achieve the final shaver blade opening with a perimeter cutting surface 104 and a cutting edge 106.

While the invention has been described as having specific embodiments, it will be understood that it is capable of further modifications. This application is, therefore, intended to cover any variations, uses, or adaptations of the invention following the general principles thereof and including such departures from the present disclosure as come within known or customary practices in the art to which this invention pertains and fall within the limits of the appended claims.

What is claimed is:

1. A process of forming a shaver blade from an elongate metal cylindrical tube having a longitudinal axis, a first longitudinal end and a second longitudinal end opposite said first end, said process comprising the steps of:

cutting said tube first longitudinal end for creating an opening extending between an outside area located longitudinally apart from an inside area, said outside area located furthest from said tube second longitudinal end;

inserting a mandrel having a working end into said tube with said working end adjacent said tube opening;

forcing a first die shape on said tube first longitudinal end and said mandrel working end and forming said tube first longitudinal end therebetween and defining a shaver blade opening; and, wherein prior to the step of forcing a first die shape, supporting die is placed around said elongate tube near said first longitudinal end.

2. The shaver blade forming process of claim 1, wherein said first die shape is forced onto said tube first longitudinal end and said mandrel working end in a substantially perpendicular direction with respect to said tube longitudinal axis.

3. The shaver blade forming process of claim 2, wherein, prior to said step of forcing a first die shape, said outside area of said tube is located coplanar with said perpendicular direction of motion of said first die shape.

4. The shaver blade forming process of claim 2, further comprising, after the step of forcing a first die shape, the step of edgeforming a shaver blade opening perimeter shape.

5. The shaver blade forming process of claim 1, further comprising, after the step of forcing a first die shape, the step of edgeforming a shaver blade opening perimeter shape.

6. The shaver blade forming process of claim 1, wherein, during the step of cutting, said tube first longitudinal end is cut with said outside area apart from said inside area a distance longitudinally a least as far as the inside radius of said elongate tube.

7. A process of forming a shaver blade from an elongate metal cylindrical tube having a longitudinal axis, a first longitudinal end and a second longitudinal end opposite said first end, said process comprising the steps of:

cutting said tube first longitudinal end for creating an opening extending between an outside area located longitudinally apart from an inside area, said outside area located furthest from said tube second longitudinal end;

inserting a mandrel having a working end into said tube with said working end adjacent said tube opening;

forcing a first die shape on said tube first longitudinal end and said mandrel working end and forming said tube first longitudinal end therebetween and defining a shaver blade opening;

wherein said first die shape is forced onto said tube first longitudinal end and said mandrel working end in a substantially perpendicular direction with respect to said tube longitudinal axis;

wherein, prior to said step of forcing a first die shape, said outside area of said tube is located coplanar with said perpendicular direction of motion of said first die shape; and, after the step of forcing a first die shape, the step of forcing a second die shape on said tube first longitudinal end and said mandrel working end in a direction substantially parallel to said tube longitudinal axis, and further forming said tube first longitudinal end and further defining said shaver blade opening.

8. The shaver blade forming process of claim 7, further comprising, after the step of forcing a second die shape, the step of edgeforming a shaver blade opening perimeter shape.

9. The shaver blade forming process of claim 8, further comprising, prior to the step of forcing a first die shape, the step of placing a supporting die around said elongate tube near said first longitudinal end.

10. The shaver blade forming process of claim 9, wherein said mandrel working end and said first and second dies are generally sphere shaped for forming said tube longitudinal end into a least a partial sphere shape.

11. The shaver blade forming process of claim 10, wherein said sphere shaped working end of said mandrel includes an annular area of tangency whereat said sphere shaped working end meets a rod shaped mandrel body, and wherein said mandrel is located with said annular area of tangency adjacent said tube first longitudinal end inside area.

12. The shaver blade forming process of claim 11, wherein, during the step of cutting, said tube first longitudinal end is cut with said outside area apart from said inside area a distance longitudinally a least as far as the inside radius of said elongate tube.

13. A process of forming a shaver blade from an elongate metal cylindrical tube having a longitudinal axis, a first longitudinal end and a second longitudinal end opposite said first end, said process comprising the steps of:

cutting said tube first longitudinal end for creating an opening extending between an outside area located longitudinally apart from an inside area, said outside area located furthest from said tube second longitudinal end;

inserting a mandrel having a working end into said tube with said working end adjacent said tube opening;

forcing a first die shape on said tube first longitudinal end and said mandrel working end and forming said tube first longitudinal end therebetween and defining a shaver blade opening;

wherein said first die shape is forced onto said tube first longitudinal end and said mandrel working end in a substantially perpendicular direction with respect to said tube longitudinal axis; and, after the step of forcing a first die shape, the step of forcing a second die shape on said tube first longitudinal end and said mandrel working end in a direction substantially parallel to said tube longitudinal axis, and further forming said tube first longitudinal end and further defining said shaver blade opening.

14. The shaver blade forming process of claim 13, further comprising, after the step of forcing a second die shape, the step of edgeforming a shaver blade opening perimeter shape.

15. The shaver blade forming process of claim 14, further comprising, prior to the step of forcing a first die shape, the step of placing a supporting die around said elongate tube near said first longitudinal end.

16. A process of forming a shaver blade from an elongate metal cylindrical tube having a longitudinal axis, a first longitudinal end and a second longitudinal end opposite said first end, said process comprising the steps of:

cutting said tube first longitudinal end for creating an opening extending between an outside area located longitudinally apart from an inside area, said outside area located furthest from said tube second longitudinal end;

inserting a mandrel having a working end into said tube with said working end adjacent said tube opening;

forcing a first die shape on said tube first longitudinal end and said mandrel working end and forming said tube first longitudinal end therebetween and defining a shaver blade opening; and, after the step of forcing a first die shape, the step of forcing a second die shape on said tube first longitudinal end and said mandrel working end and further forming said tube first longitudinal end and further defining said shaver blade opening.

17. The shaver blade forming process of claim 16, further comprising, after the step of forcing a second die shaped, the step of edgeforming a shaver blade opening perimeter shape.

18. The shaver blade forming process of claim 17, further comprising, prior to the step of forcing a first die shape, the step of placing a supporting die around said elongate tube near said first longitudinal end.

19. A process of forming a shaver blade from an elongate metal cylindrical tube having a longitudinal axis, a first longitudinal end and a second longitudinal end opposite said first end, said process comprising the steps of:

cutting said tube first longitudinal end for creating an opening extending between an outside area located longitudinally apart from an inside area, said outside area located furthest from said tube second longitudinal end;

inserting a mandrel having a working end into said tube with said working end adjacent said tube opening;

forcing a first die shape on said tube first longitudinal end and said mandrel working end and forming said tube first longitudinal end therebetween and defining a shaver blade opening; and, wherein said mandrel working end and said first die are generally sphere shaped for forming said tube first longitudinal end into at least a partial sphere shape.

20. The shaver blade forming process of claim 19, wherein said sphere shaped working end of said mandrel includes an annular area of tangency whereat said sphere shaped working end meets a rod shaped mandrel body, and wherein said mandrel is located with said annular area of tangency adjacent said tube first longitudinal end inside area.

21. The shaver blade forming process of claim 20, wherein, during the step of cutting, said tube first longitudinal end is cut with said outside area apart from said inside area a distance longitudinally a least as far as the inside radius of said elongate tube.

22. A process of forming a shaver blade from an elongate metal cylindrical tube having a longitudinal axis, a first longitudinal end and a second longitudinal end opposite said first end, said process comprising the steps of:

cutting said tube first longitudinal end for creating an opening extending between an outside area located longitudinally apart from an inside area, said outside area located furthest from said tube second longitudinal end;

inserting a mandrel having a working end into said tube longitudinally through said tube second longitudinal end and with said working end adjacent said tube opening; and, forcing a first die shape on said tube first longitudinal end and said mandrel working end and forming said tube first longitudinal end therebetween and defining a shaver blade opening.

* * * * *